United States Patent
Zhang et al.

(10) Patent No.: US 10,690,649 B2
(45) Date of Patent: Jun. 23, 2020

(54) SUPERCRITICAL CO2 REACTOR AND TEST SYSTEM OF CREEPAGE, DIFFUSION AND EROSION OF ROCK MASS

(71) Applicant: Taiyuan University of Technology, Taiyuan, Shanxi (CN)

(72) Inventors: Chunwang Zhang, Shanxi (CN); Zhixin Jin, Shanxi (CN); Guorui Feng, Shanxi (CN); Xuanmin Song, Shanxi (CN)

(73) Assignee: Taiyuan University of Technology, Taiyuan (CN)

( * ) Notice: Subject to any disclaimer, the term of this patent is extended or adjusted under 35 U.S.C. 154(b) by 37 days.

(21) Appl. No.: 16/217,031

(22) Filed: Dec. 11, 2018

(65) Prior Publication Data
US 2019/0204288 A1 Jul. 4, 2019

(30) Foreign Application Priority Data
Dec. 28, 2017 (CN) .......................... 2017 1 1456201

(51) Int. Cl.
*G01N 33/24* (2006.01)
*G01N 3/56* (2006.01)
(Continued)

(52) U.S. Cl.
CPC .............. *G01N 33/24* (2013.01); *G01N 3/00* (2013.01); *G01N 3/10* (2013.01); *G01N 3/12* (2013.01);
(Continued)

(58) Field of Classification Search
CPC .. E02D 1/027; G01N 3/24; G01N 2203/0256; G01N 2203/0254
See application file for complete search history.

(56) References Cited

U.S. PATENT DOCUMENTS 3,457,777 A * 7/1969 Nielsen ............... G01N 3/08
73/84
3,635,078 A * 1/1972 Wissa ................. G01N 3/08
73/790
(Continued)

FOREIGN PATENT DOCUMENTS

CN 101592574 A1 * 12/2009
CN 201464298 U * 5/2010
(Continued)

OTHER PUBLICATIONS

Mattson et al., "EGS Rock Reactions with Supercritical CO2 Saturated with Water and Water Saturated with CO2", Proceedings from the 38th Workshop on Geothermal Reservoir Engineering, Feb. 2013. (Year: 2013).*
(Continued)

*Primary Examiner* — David A Rogers
(74) *Attorney, Agent, or Firm* — Wayne & Ken, LLC; Tony Hom

(57) ABSTRACT

A supercritical CO2 reactor and a test system of creepage, diffusion and erosion of rock mass. The supercritical CO2 reactor includes a reactor body having a test chamber, a heating layer arranged in a side wall of the reactor body, a temperature sensor and a pressure sensor arranged in the test chamber, a sealing cover configured to seal an opening of the reactor body, a fixing component arranged on the sealing cover, a hydraulic loading component configured to apply an axial load on the specimen. The reactor body is provided with an air inlet/outlet pipe configured to communicate the test chamber with external environment. The air inlet/outlet pipe is provided with a air valve, and the fixing component includes vertical guide bars, an upper pad and a lower pad slideably arranged on the vertical guide bars. The hydraulic
(Continued)

loading component includes a oil-loading tank and an axial loading rod.

10 Claims, 2 Drawing Sheets

(51) Int. Cl.
  *G01N 15/08* (2006.01)
  *G01N 3/12* (2006.01)
  *G01N 17/00* (2006.01)
  *G01N 3/18* (2006.01)
  *G01N 3/00* (2006.01)
  *G01N 3/10* (2006.01)

(52) U.S. Cl.
  CPC .............. *G01N 3/18* (2013.01); *G01N 3/567* (2013.01); *G01N 15/082* (2013.01); *G01N 15/0806* (2013.01); *G01N 17/00* (2013.01)

(56) References Cited

U.S. PATENT DOCUMENTS

| | | | | |
|---|---|---|---|---|
| 3,934,455 | A * | 1/1976 | Harrisberger | G01N 15/082 436/5 |
| 4,122,704 | A * | 10/1978 | Lutenegger | G01N 3/10 73/822 |
| 4,715,212 | A * | 12/1987 | Johanson | G01N 3/08 73/38 |
| 4,885,941 | A * | 12/1989 | Vardoulakis | G01N 3/08 73/794 |
| 5,005,403 | A * | 4/1991 | Steudle | G01N 13/04 73/61.71 |
| 5,009,512 | A * | 4/1991 | Lessi | G01B 7/16 374/6 |
| 5,025,668 | A * | 6/1991 | Sarda | G01N 3/10 73/795 |
| 5,063,785 | A * | 11/1991 | Labuz | G01N 3/10 73/821 |
| 5,161,407 | A * | 11/1992 | Ankeny | G01N 15/0893 73/38 |
| 5,226,310 | A * | 7/1993 | Steiger | E21B 49/006 73/38 |
| 5,275,063 | A * | 1/1994 | Steiger | G01N 33/241 73/865.6 |
| 5,289,728 | A * | 3/1994 | Johanson | G01N 3/10 73/866 |
| 5,323,655 | A * | 6/1994 | Eagan | G01N 1/286 73/432.1 |
| 6,289,725 | B1 * | 9/2001 | Hubbell | G01N 15/08 141/47 |
| 6,718,835 | B2 * | 4/2004 | Wang | E02D 1/027 73/38 |
| 6,729,189 | B2 * | 5/2004 | Paakkinen | G01N 3/02 73/813 |
| 6,799,471 | B1 * | 10/2004 | Regimand | G01N 3/36 137/386 |
| 7,143,653 | B2 * | 12/2006 | Abdel-Hadi | G01N 3/10 73/819 |
| 7,549,315 | B2 * | 6/2009 | Bulled | G01N 3/10 73/11.01 |
| 8,438,914 | B2 * | 5/2013 | Martiska | G01N 3/08 73/788 |
| 8,800,353 | B2 * | 8/2014 | Ng | G01N 33/24 73/73 |
| 9,038,477 | B2 * | 5/2015 | Yuers | G01N 33/38 73/803 |
| 9,316,572 | B2 * | 4/2016 | Benet | G01N 3/08 |
| 9,377,392 | B2 * | 6/2016 | Rickards | G01N 19/00 |
| 9,383,346 | B2 * | 7/2016 | Gupta | G01N 33/24 |
| 9,546,940 | B2 * | 1/2017 | Gupta | G01N 33/24 |
| 10,048,183 | B2 * | 8/2018 | Ni | G01N 3/24 |
| 10,365,193 | B2 * | 7/2019 | Feng | G01N 3/12 |
| 10,472,788 | B2 * | 11/2019 | Wang | E02D 3/10 |
| 10,564,079 | B2 * | 2/2020 | Ma | G01N 33/24 |
| 2008/0060444 | A1 * | 3/2008 | Conway | G01N 3/08 73/821 |
| 2011/0214506 | A1 * | 9/2011 | Khoury | G01N 33/24 73/784 |
| 2015/0268217 | A1 * | 9/2015 | Gupta | G01N 33/24 73/819 |

FOREIGN PATENT DOCUMENTS

| | | | | |
|---|---|---|---|---|
| CN | 102128741 | A1 * | 7/2011 | |
| CN | 106885740 | A1 * | 6/2017 | |
| EP | 0349422 | B1 * | 2/1992 | G01N 3/10 |
| RO | 106807 | B1 * | 6/1993 | |
| SU | 491080 | A1 * | 2/1976 | |
| SU | 924240 | A1 * | 4/1982 | |
| SU | 730079 | A1 * | 12/1984 | |
| SU | 1262332 | A1 * | 10/1986 | |

OTHER PUBLICATIONS

Pruess et al., "On the Feasibility of Using Supercritical CO2 as heat Transmission Fluid in an Engineered Hot Dry Rock Geothermal System", Proceedings from the 31st Workshop on Geothermal Reservoir Engineering, Jan. 2006. (Year: 2006).*

Hu et al., "Fracture Initiation of an Inhomogeneous Shale Rock under a Pressurized Supercritical CO2 Jet", Applied Sciences, Oct. 23, 2017. (Year: 2017).*

Wang et al., "Design of Experimental System for Supercritical CO2 Fracturing Under Confining Pressure Conditions", IOP Publishing, Mar. 22, 2018. (Year: 2018).*

* cited by examiner

SUPERCRITICAL CO2 REACTOR AND TEST SYSTEM OF CREEPAGE, DIFFUSION AND EROSION OF ROCK MASS

CROSS-REFERENCE TO RELATED APPLICATIONS

This application claims to Chinese Application No. 201711456201.2 with a filing date of Dec. 28, 2017. The content of the aforementioned application, including any intervening amendments thereto, is incorporated herein by reference.

TECHNICAL FIELD

The present disclosure relates to a rock mass test technology, and more particularly to a supercritical $CO_2$ reactor and a test system of creepage, diffusion and erosion of rock mass.

BACKGROUND

The critical pressure and critical temperature of $CO_2$ are 7.39 MPa and 31.06° C., respectively. When the $CO_2$ is in an environment where the temperature and pressure exceed the critical temperature and the critical pressure, it enters a supercritical state. The supercritical $CO_2$ is a supercritical fluid which is neither a air nor a liquid, and has both characteristics of a large solubility of liquid solute and easy to diffuse and flow of air. It has aroused extensive attention and is being applied to various fields due to its characters of cheap, easy to gain, non-toxic, pollution-free and uninflammable.

With the development of exploration technology of unconventional oil-gas resources and underground storage technology, the supercritical $CO_2$ has been widely applied. For example, the coal-bed methane is exploited by injecting the supercritical $CO_2$, and a supercritical $CO_2$ cannon is used for deep-hole blasting and permeability increasing in exploitation of the oil-gas resources. For another example, injecting liquid $CO_2$ into unminable coal layer by technology of underground $CO_2$ storage can not only sequestrate $CO_2$, but also separate gas from coal body so as to increase gas production. For yet another example, $CO_2$ can be injected into an abandoned mine chamber to seal the mine. As the storage depth of $CO_2$ increases, the pressure and temperature will also increase accordingly. It is easy to reach the critical pressure and temperature of $CO_2$. In order to better realize application and development of the supercritical $CO_2$, it is very important to fully understand and master the mechanical properties of the rock mass under the condition of the supercritical $CO_2$. For $CO_2$ sequestration, it is of great significance for the preparation and design of the underground sequestration scheme, instruction of on-site construction and later maintenance to understand of creepage, diffusion and erosion reaction of the rock mass in a multi-field coupled environment of stress-temperature-supercritical $CO_2$ fluid and under a long-term thermo-mechanical coupling effects.

In current study, relevant seepage diffusion theory and numerical simulation are difficult to accurately predict the creepage, diffusion and erosion of the rock mass in the supercritical $CO_2$ environment. At present, the laboratory test is still a usual means. For example, a test of the creepage, diffusion and erosion reaction of the rock mass is conducted by immersing a cylindrical specimen of rock mass into the supercritical $CO_2$ environment for a preset time beforehand, then removing the specimen to a triaxial experimental machine and applying an axial load on the specimen, and at last applying a confining pressure on the specimen by injecting oil. However, the specimen has been out of the supercritical $CO_2$ environment when the test is conducted, resulting a relatively larger error of the test result.

SUMMARY

An object of the present application is to provide a supercritical $CO_2$ reactor for providing a supercritical $CO_2$ environment for a test of creepage, diffusion and erosion reaction of a rock mass under a triaxial stress state. Another object is to provide a test system for creepage, diffusion and erosion of rock mass. The test system provides a experimental basis for the long-term research of mechanical property of the rock mass under a multifield coupled environment of stress-temperature-supercritical $CO_2$ fluid and a environment of different load, different temperature and different confining pressure on the base of the supercritical $CO_2$ reactor of the supercritical $CO_2$.

The present application provides a supercritical $CO_2$ reactor for providing a supercritical $CO_2$ environment to a specimen. The supercritical $CO_2$ reactor includes a reactor body having a test chamber, a heating layer arranged in a side wall of the reactor body, a temperature sensor and a pressure sensor arranged in the test chamber, a sealing cover configured to seal an opening of the reactor body, a fixing component arranged on the sealing cover and a hydraulic loading component configured to apply an axial load on the specimen. The reactor body is provided with an air inlet/outlet pipe configured to communicate the test chamber with external environment, and the air inlet/outlet pipe is provided with an air valve. The fixing component comprises at least two vertical guide bars, and an upper pad and a lower pad slidably arranged on the vertical guide bars. A first end of each vertical guide bar is connected to a lower surface of the sealing cover, and a second end of the vertical guide bar is provided with a limit part. The vertical guide bars, the upper pad and the lower pad form a fixing area. The hydraulic loading component comprises an oil-loading tank and an axial loading rod. The oil-loading tank is sealingly arranged on an upper surface of the sealing cover and provided with an oil inlet pipe having an oil valve. A first end of the axial loading rod is slidably arranged in the oil-loading tank, and a second end of the axial loading rod passes through the sealing cover and faces the upper pad. The axial loading rod is in sealed contact with the oil-loading tank and the sealing cover.

Further, the reactor body is provided with a lead wire hole for connection of the temperature sensor and/or the pressure sensor.

Further, an end face of the opening of the reactor body is provided with a plurality of threaded holes extending in an axial direction. The sealing cover is provided with a plurality of connecting holes axially penetrating the sealing cover and corresponding the threaded holes. A sealing washer is arranged between the reactor body and the sealing cover and is fixed by a plurality of bolts.

Further, the supercritical $CO_2$ reactor further comprises an insulating layer, and the insulating layer encloses the reactor body and is higher than the open end face of the reactor body at a distance of 10-20 mm.

Further, the upper pad and the lower pad each comprise a connecting part connected to the vertical guide bars and a fixing part configured to fix the specimen. The connecting part and the fixing part are both cylindrical. A radius of the connecting part is at least the sum of a diameter of the vertical guide bar and a radius of the fixing part.

Further, the first end of the vertical guide bar is in threaded connection with the sealing cover. The limit part is a limit nut threaded to the vertical guide bar.

Further, the oil-loading tank is in threaded connection with the sealing cover.

Further, two positioning pivot rods are symmetrically provided on the sealing cover.

Further, the air inlet/outlet pipe and the oil inlet pipe are both stainless steel pipes. The air valve and the oil valve are both stainless needle valves and are connected with the stainless steel pipes through adjustable thread joints.

The disclosure further provides a test system for creepage, diffusion and erosion of rock mass, including a hydraulic loading system, an intelligent temperature control system, a temperature-pressure monitoring system, a $CO_2$ injection system, a vacuuming system and the supercritical $CO_2$ reactor. The oil inlet pipe is connected to the hydraulic loading system. The heating layer is connected to the intelligent temperature control system. The temperature sensor and pressure sensor are connected to the temperature-pressure monitoring system. The air inlet/outlet pipe is connected to the $CO_2$ injection system or the vacuuming system. The temperature-pressure monitoring system is configured to detect a temperature and a pressure value in the test chamber to feed back the detected temperature to the intelligent temperature control system and display the detected pressure in real time. The intelligent temperature control system is configured to control a heating temperature of the heating layer according to the detected temperature.

The supercritical $CO_2$ reactor of the present invention has following advantages compared to the prior arts.

The specimen is placed in the fixing area and fixed by sliding the upper pad. Oil is injected into the oil-loading tank through the oil inlet pipe. The upper pad is applied with an axial load by pushing the axial loading rod until the axial load reaches a preset value. The specimen then is placed in the test chamber, and the opening of reactor body is sealed by the sealing cover. The test chamber is heated by the heating layer, and air in the test chamber is ejected through the inlet/outlet pipe to form a negative pressure condition in the test chamber. $CO_2$ is injected into the test chamber though the inlet/outlet pipe, and the temperature and pressure in the test chamber are monitored by the temperature sensor and the pressure sensor, respectively to determine whether the critical temperature and the critical pressure are reached so as to determine the supercritical $CO_2$ environment. If there is a supercritical $CO_2$ environment, the test of creepage, diffusion and erosion of the rock mass under the triaxial stress state can be conducted directly in the reactor. Therefore, the supercritical $CO_2$ reactor provides the supercritical $CO_2$ environment for the test of creepage, diffusion and erosion of the rock mass under the triaxial stress state. The test system adopts the hydraulic loading system to apply the axial load to the specimen and the $CO_2$ injection system to apply the confining pressure load to the specimen so as to form the triaxial stress state of the specimen. In particular, compared to other ways to apply the confining pressure load, such manner does not need tedious pre-treatment measures on the specimen in the early stage. Meanwhile, the test system can change load values, temperature and confining pressure to provide an experimental basis for a long-term mechanical property research of the rock mass under a multi-field coupling environment of stress-temperature-supercritical $CO_2$ fluid and a environment of different load, different temperature and different confining pressure.

Figure 1:
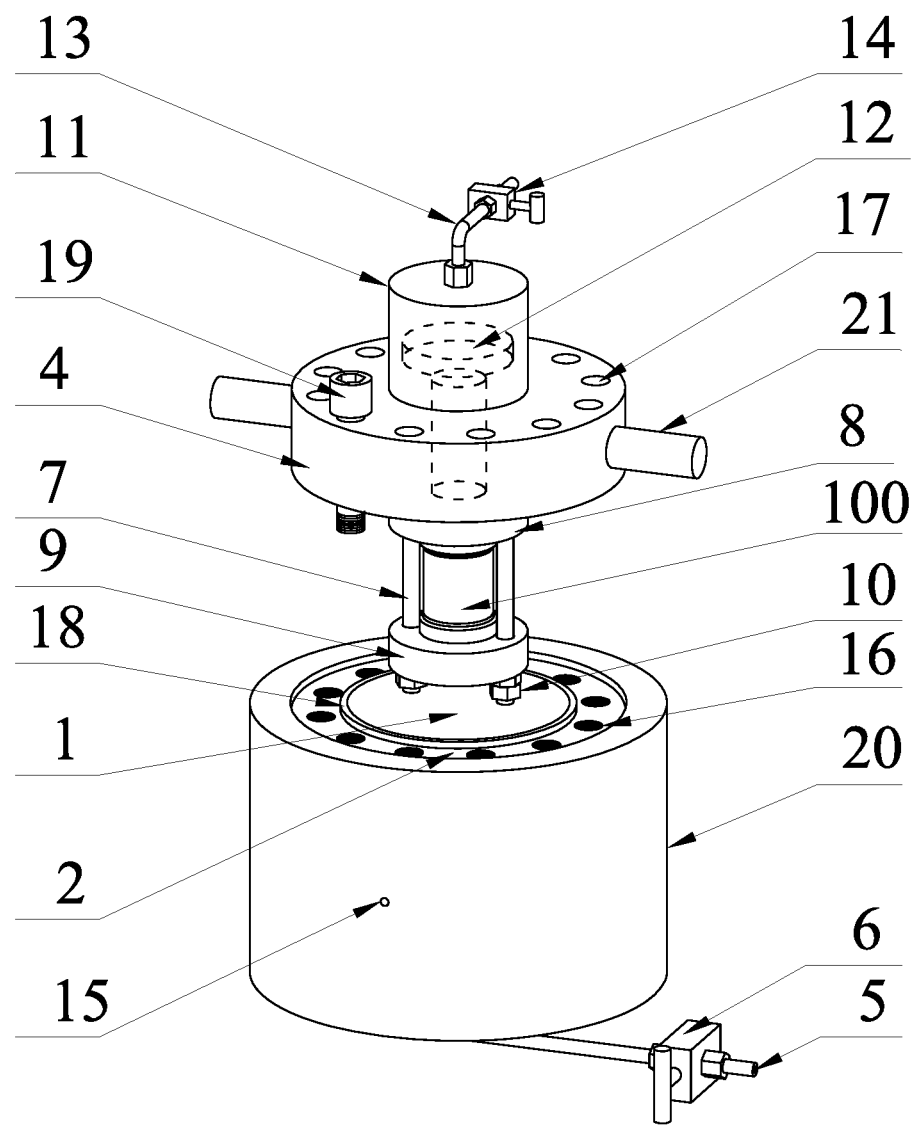
FIG. 1 is a schematic diagram of a supercritical $CO_2$ reactor according to a first embodiment.
Figure 2:
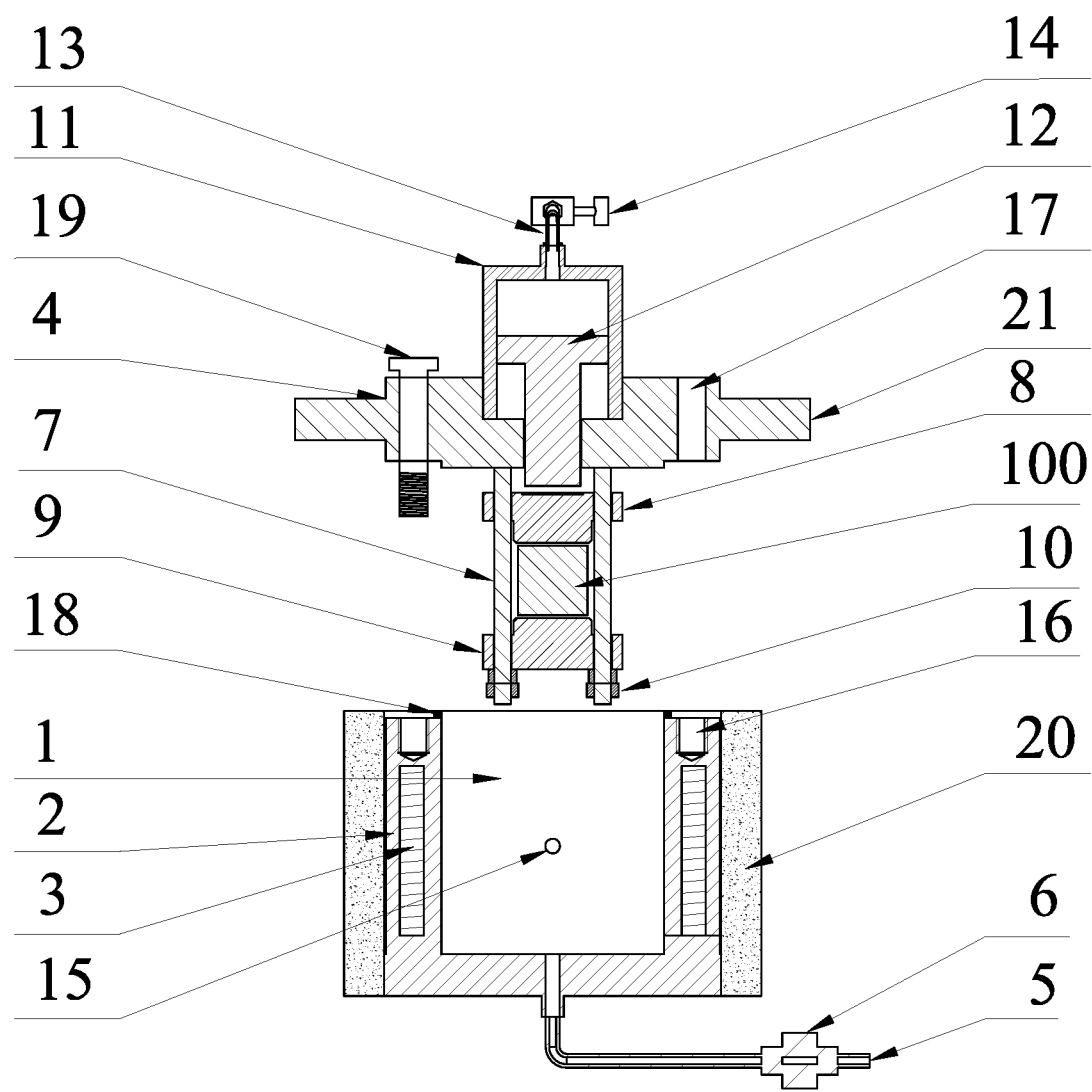
FIG. 2 is a sectional view of the supercritical $CO_2$ reactor in FIG. 1.

REFERENCE NUMERALS 1, test chamber; 2, reactor body; 3, heating layer; 4, sealing cover; 5, air inlet/outlet pipe; 6, air valve; 7, vertical guide bar; 8, upper pad; 9, lower pad; 10, limit part; 11, oil-loading tank; 12, axial loading rod; 13, oil inlet pipe; 14, oil valve; 15, lead wire hole; 16, threaded hole; 17, connecting hole; 18, sealing washer; 19, bolt; 20, insulating layer; 21, positioning pivot rod; 100, specimen.

DETAILED DESCRIPTION OF EMBODIMENTS

Example 1

The present embodiment provides a supercritical $CO_2$ reactor used for providing a supercritical $CO_2$ environment to a specimen. The supercritical $CO_2$ reactor includes a reactor body 2 having a test chamber 1, a heating layer 3 arranged in a side wall of the reactor body 2, a temperature sensor and a pressure sensor arranged in the test chamber 1, a sealing cover 4 configured to seal an opening of the reactor body 2, a fixing component arranged on the sealing cover 4 and a hydraulic loading component configured to apply an axial load on the specimen 100. The reactor body 2 is provided with an air inlet/outlet pipe 5 configured to communicate the test chamber 1 with an external environment, and the inlet/outlet pipe 5 is provided with an air valve 6. The fixing component includes at least two vertical guide bars 7, and an upper pad 8 and a lower pad 9 slidably arranged on the vertical guide bars 7. A first end of the vertical guide bar 7 is connected to a lower surface of the sealing cover 4. A second end of the vertical guide bar 7 is provided with a limit part 10 configured to limit the lower pad 9. The vertical guide bar 7, the upper pad 8 and lower pad 9 form a fixing area. The hydraulic loading component includes an oil-loading tank 11 and an axial loading rod 12. The oil-loading tank 11 is sealingly arranged on an upper surface of the sealing cover 4 and provided with an oil inlet pipe 13 having an oil valve 14. A first end of the axial loading rod 12 is slidably arranged in the oil-loading tank 11. A second end of the axial loading rod 12 passes through the sealing cover 4 and faces the upper pad 8. The axial loading rod 12 is in sealed contact with the oil-loading tank 11 and sealing cover 4.

The specimen 100 is placed in the fixing area and fixed by sliding the upper pad 8. Oil is injected into the oil-loading tank 11 through the oil inlet pipe 13. The upper pad 8 is applied with an axial load by pushing the axial loading rod 12 until the axial load reaches a preset value. The specimen 100 then is placed in the test chamber 1, and the opening of reactor body 2 is sealed by the sealing cover 4. The test chamber 1 is heated by the heating layer 3, and the air in the test chamber 1 is ejected through the air inlet/outlet pipe 5 to form a negative pressure condition in the test chamber 1. $CO_2$ is injected into the test chamber 1 though the air inlet/outlet pipe 5, and the temperature and pressure in the test chamber 1 are monitored by the temperature sensor and the pressure sensor, respectively to determine whether the critical temperature and the critical pressure are reached so as to determine the supercritical $CO_2$ environment. If there is a supercritical $CO_2$ environment, the test of creepage, diffusion and erosion of the rock mass under the triaxial stress state can be carried out directly in the supercritical $CO_2$ reactor.

Further, the test chamber 1 is cylindrical. The heating layer 3 is electric. The temperature sensor is a thermocouple sensor.

Further, the reactor body 2 is provided with a lead wire hole 15 for connection of the temperature sensor and/or the pressure sensor, so as to connect the temperature sensor and/or the pressure sensor to an temperature-pressure monitoring system. One or two lead wire holes 15 can be arranged. If there is only one lead wire hole 15, two lead wires of the temperature sensor and the pressure sensor both pass though the lead wire hole 15. If there are two lead wire holes 15, the two leads of the temperature sensor and the pressure sensor can pass though the two lead wire holes 15, respectively.

Further, an end surface of the opening of the reactor body 2 is provided with a plurality of threaded holes 16 extending in an axial direction. The sealing cover 4 is provided with a plurality of connecting holes 17 axially penetrating the sealing cover 4 and corresponding the threaded holes 16. A sealing washer 18 is arranged between the reactor body 2 and the sealing cover 4 and is fixed by a plurality of bolts 19. Preferably, the sealing washer 18 is made of polytetrafluoroethylene. Polytetrafluoroethylene is a polymer polymerized by tetrafluoroethylene, with excellent chemical stability, corrosion resistance, airtightness, high lubrication, non-viscous, electrical insulation, good aging resistance and wide temperature resistance (it can work under a temperature range of +250° C.~-180° C. for a long time).

Further, the test chamber 1 includes an insulating layer 20 which is higher than the open end face of the reactor body 2 at a distance of 10-20 mm, so that the insulating layer 20 is able to enclose the sealing cover 4 partly, improving airtightness between the sealing cover 4 and the reactor body 2. Preferably, the insulating layer 20 is made of asbestos.

Further, the upper pad 8 and the lower pad 9 each include a connecting part connected to the vertical guide bars 7 and a fixing part configured to fix the specimen 100. The connecting part and fixing part are both cylindrical. A radius of the connecting part is at least the sum of a diameter of the vertical guide bar 7 and a radius of the fixing part, so that the vertical guide bars 7 may pass through the connecting part.

A first end of the vertical guide bar 7 may be welded or clamped on the sealing cover 4. Preferably, the first end of the vertical guide bar 7 is in threaded connection with the sealing cover 4. Thread is easy to process, install and disassemble and has a stable connection. The limit part 10 may be welded on the vertical guide bar 7 or formed in one body with the vertical guide bar 7. Preferably, the limit part 10 is a limit nut in threaded connection with the vertical guide bar 7, so that the upper pad 8 and the lower pad 9 are easily installed and the height of the lower pad 9 is adjusted.

In order to easily install and disassemble, the oil-loading tank 11 is detachably installed on the sealing cover 4. Specifically, the oil-loading tank 11 is in threaded connection with the sealing cover 4, so that an leak tightness between the oil-loading tank 11 and the sealing cover 4 is ensured.

Further, the sealing cover 4 is symmetrically provided with two positioning pivot rods 21.

Further, the air inlet/outlet pipe 5 and the oil inlet pipe 13 both are stainless steel pipes. The air valve 6 and the oil valve 14 are both stainless needle valves and are connected with the stainless steel pipes through adjustable thread joints. The stainless needle valve has a high resistance to high temperature and high pressure and a good airtightness. The adjustable thread joints can ensure an airtightness of joints during opening or closing the pipe pathways.

Example 2

This embodiment bases on the embodiment 1 and further provides specific designing parameters.

An inner diameter of the test chamber 1 ranges from 80 mm to 120 mm. A height of the test chamber 1 ranges from 160 mm to 200 mm. A diameter of the sealing cover 4 ranges from 150 mm to 180 mm. A thickness of the sealing cover 4 ranges from 20 mm to 50 mm. An edge of the sealing cover 4 is provided with 12 connecting holes 17, central axes of the connecting holes 17 are parallel to a central axis of the sealing cover 4. Diameters of the connecting holes 17 correspond to the sizes of the bolts 19. A depth of the threaded holes 16 ranges from 15 mm to 25 mm. The bolts 19 are hexagon socket bolts. A thickness of the sealing washer 18 ranges from 3 mm to 5 mm. The heating layer 3 is evenly arranged in the inner wall of the reactor body 2, is equal in height to the test chamber 1 and has a thickness of 30 mm. The oil-loading tank 11 has a inner diameter of 50 mm and a wall thickness of 5 mm-10 mm. The axial loading rod 12 has a sliding range of 20 mm-35 mm. The vertical guide bar 7 is a cylindrical bar having a diameter of 10 mm-20 mm and a length of 130 mm-180 mm. The limit part 10 is a hexagon nut. The fixing part has a diameter of 50 mm and a height of 10 mm-20 mm. The connecting part has a diameter of 80 mm-100 mm and a height of 15 mm-30 mm. The insulating layer 20 has a thickness of 30 mm and is higher than the reactor body 2 at a distance of 10-20 mm.

Example 3

This embodiment provides a test system of creepage, diffusion and erosion of rock mass, including a hydraulic loading system, a intelligent temperature control system, a temperature-pressure monitoring system, a $CO_2$ injection system, a vacuuming system and the supercritical $CO_2$ supercritical $CO_2$ reactor in the example 1. The oil inlet pipe 13 is connected to the hydraulic loading system. The heating layer 3 is connected to the intelligent temperature control system. The temperature sensor and pressure sensor are connected to the temperature-pressure monitoring system. The air inlet/outlet pipe 5 is connected to the $CO_2$ injection system or the vacuuming system. The temperature-pressure monitoring system is configured to detect temperature and pressure in the test chamber 1 to feed back the detected temperature to the intelligent temperature control system and display the detected pressure in real-time. The intelligent temperature control system control is configured to control a heating temperature of the heating layer 3 based on the detected temperature.

In this embodiment, the vacuuming system includes a vacuum pump. The $CO_2$ injection system includes a plunger pump. The temperature in the test chamber 1 varies from 20° C. to 400° C., and the pressure in the test chamber l varies from 5 MPa-40 MPa. The oil-loading tank 11 is able to provide a maximum load of 40 MPa.

It should be understood that for those of ordinary skills in the art, improvements or variations can be made based on the above descriptions, and such improvements and variations fall within the scope of the appended claims.

The embodiments are only illustrative of the present disclosure, and apparently the implementations are not limited by the above modes. The embodiments described herein and various modifications based on the ideas and technical solutions of the present disclosure fall within the scope of the present application.

What is claimed is:

1. A supercritical $CO_2$ reactor for providing a supercritical $CO_2$ environment to a specimen, comprising:
   a reactor body having a test chamber,
   a heating layer arranged in a side wall of the reactor body,
   a temperature sensor and a pressure sensor arranged in the test chamber,
   a sealing cover configured to seal an opening of the reactor body,
   a fixing component arranged on the sealing cover, and
   a hydraulic loading component configured to apply an axial load on the specimen; wherein
   the reactor body is provided with an air inlet/outlet pipe configured to communicate the test chamber with an external environment;
   the air inlet/outlet pipe is provided with an air valve;
   the fixing component comprises at least two vertical guide bars, and an upper pad and a lower pad slidably arranged on each of the vertical guide bars;
   a first end of each vertical guide bar is connected to a lower surface of the sealing cover; a second end of each vertical guide bar is provided with a limit part;
   the vertical guide bar, the upper pad and the lower pad form a fixing area;
   the hydraulic loading component comprises an oil-loading tank and an axial loading rod;
   the oil-loading tank is sealingly arranged on an upper surface of the sealing cover and provided with an oil inlet pipe;
   the oil inlet pipe is provided with an oil valve;
   a first end of the axial loading rod is slidably arranged in the oil-loading tank; a second end of the axial loading rod passes through the sealing cover and faces the upper pad; and the axial loading rod is in sealed contact with the oil-loading tank and the sealing cover.

2. The supercritical $CO_2$ reactor of claim 1, wherein the reactor body is provided with a lead wire hole for connection of the temperature sensor and/or the pressure sensor.

3. The supercritical $CO_2$ reactor of claim 1, wherein
   an end face of the opening of the reactor body is provided with a plurality of threaded holes extending in an axial direction;
   the sealing cover is provided with a plurality of connecting holes axially penetrating the sealing cover and corresponding the threaded holes; and
   a sealing washer is arranged between the reactor body and the sealing cover and is fixed by a plurality of bolts.

4. The supercritical $CO_2$ reactor of claim 1, wherein the supercritical $CO_2$ reactor further comprises an insulating layer, and the insulating layer encloses the reactor body and is higher than the open end face of the reactor body at a distance of 10-20 mm.

5. The supercritical $CO_2$ reactor of claim 1, wherein the upper pad and the lower pad each comprise a connecting part connected to the vertical guide bars and a fixing part configured to fix the specimen; the connecting part and the fixing part are both cylindrical; and a radius of the connecting part is at least a sum of a diameter of the vertical guide bar and a radius of the fixing part.

6. The supercritical $CO_2$ reactor of claim 1, wherein the first end of the vertical guide bar is in threaded connection with the sealing cover; the limit part is a limit nut in threaded connection with the vertical guide bar.

7. The supercritical $CO_2$ reactor of claim 1, wherein the oil-loading tank is in threaded connection with the sealing cover.

8. The supercritical $CO_2$ reactor of claim 1, wherein two positioning pivot rods are symmetrically provided on the sealing cover.

9. The supercritical $CO_2$ reactor of claim 1, wherein the air inlet/outlet pipe and the oil inlet pipe are both stainless steel pipes, and the air valve and the oil valve are both stainless needle valves and are connected with the stainless steel pipes through adjustable thread joints.

10. A test system of creepage, diffusion and erosion of rock mass, comprising:
    a hydraulic loading system,
    an intelligent temperature control system,
    a temperature-pressure monitoring system,
    a $CO_2$ injection system,
    a vacuuming system, and
    the supercritical $CO_2$ reactor of claim 1; wherein
    the oil inlet pipe is connected to the hydraulic loading system;
    the heating layer is connected to the intelligent temperature control system;
    the temperature sensor and pressure sensor are connected to the temperature-pressure monitoring system;
    the air inlet/outlet pipe is connected to the $CO_2$ injection system or the vacuuming system;
    the temperature-pressure monitoring system is configured to detect a temperature value and a pressure value in the test chamber to feed back the detected temperature to the intelligent temperature control system and display the detected pressure in real time; and
    the intelligent temperature control system is configured to control a heating temperature of the heating layer based on the detected temperature.

* * * * *